(12) United States Patent
Wright et al.

(10) Patent No.: US 8,999,920 B2
(45) Date of Patent: Apr. 7, 2015

(54) RECONSTITUTED HIGH DENSITY LIPOPROTEIN FORMULATION AND PRODUCTION METHOD THEREOF

(75) Inventors: Samuel Wright, Westfield, NJ (US);
Martin Imboden, Münsingen (CH);
Reinhard Bolli, Guemligen (CH);
Marcel Waelchli, Gwatt (CH)

(73) Assignee: CSL Limited, Parkville, Victoria (AU)

( * ) Notice: Subject to any disclaimer, the term of this patent is extended or adjusted under 35 U.S.C. 154(b) by 0 days.

(21) Appl. No.: 13/805,488

(22) PCT Filed: Jun. 30, 2011

(86) PCT No.: PCT/AU2011/000819
§ 371 (c)(1),
(2), (4) Date: Mar. 18, 2013

(87) PCT Pub. No.: WO2012/000048
PCT Pub. Date: Jan. 5, 2012

(65) Prior Publication Data
US 2013/0190226 A1 Jul. 25, 2013

Related U.S. Application Data

(60) Provisional application No. 61/359,925, filed on Jun. 30, 2010.

(51) Int. Cl.
*A61K 38/17* (2006.01)
*A61K 9/00* (2006.01)
*A61K 9/127* (2006.01)
*A61K 31/56* (2006.01)
*A61K 31/685* (2006.01)
*A61K 45/06* (2006.01)

(52) U.S. Cl.
CPC ........... *A61K 38/1709* (2013.01); *A61K 9/0019* (2013.01); *A61K 9/1275* (2013.01); *A61K 31/56* (2013.01); *A61K 31/685* (2013.01); *A61K 45/06* (2013.01)

(58) Field of Classification Search
CPC ............... A61K 9/1275; A61K 31/56–31/569; A61K 31/66–31/6615; A61K 31/662–31/665; A61K 31/67–31/675; A61K 31/683–31/688; C07K 14/775
See application file for complete search history.

(56) References Cited

U.S. PATENT DOCUMENTS 5,652,339 A 7/1997 Lerch
2011/0087008 A1 4/2011 Brinkman et al.

FOREIGN PATENT DOCUMENTS

WO WO 2010/057203 A2 5/2010

OTHER PUBLICATIONS

Sharp et al. ("Hepatic response to parenchymal injection of sodium cholate and monooctanoin," Surgical Forum (1981), 32, 176-7).*
"Phosphatidylcholine, structure, occurrence, biochemistry and analysis" The AOCS Lipid Library, downloaded May 2, 2014 from http://lipidlibrary.aocs.org/Lipids/pc/index.htm.*
Bettini et al., "Book Reviews—Handbook of Pharmceutical Excipients, Third Ed., Arthur H. Kibbe (ed.)," European Journal of Pharmaceutics and Biopharmaceutics, vol. 50, pp. 329-330, 2000.
Assmann et al., "HDL Cholesterol and Protective Factors in Artherosclerosis," Circulation, vol. 109, pp. III-8-III-14, 2004.
Tardif et al., "Effects of Reconstituted High-Density Lipoprotein Infusions on Coronary Atherosclerosis," JAMA, vol. 297, No. 15, pp. 1675-1682, Apr. 18, 2007.
International Search Report issued on Sep. 1, 2011 in application No. PCT/AU2011/000819.
International Search Report issued in application No. PCT/AU2011/000819 on Sep. 1, 2011.
Hoffman, "The Continuing Importance of Bile Acids in Liver and Intestinal Disease," Arch Intern Med., vol. 159, pp. 2647-2658, Dec. 1999.
Nissen et al., "Effect of Recombinant ApoA-I Milano on Coronary Atherosclerosis in Patients With Acute Coronary Symptoms," JAMA, vol. 290, No. 17, pp. 2292-2300, Nov. 5, 2003.
Lerch et al., "Production and Characterization of a Reconsititured High Density Lipoprotein for Therapeutic Applications," Vox Sand, vol. 71, pp. 155-164, 1996.
Easton et al., "A Multiple Ascending Dose Study of CSL 112, an Infused Formulation of ApoA-1," The Journal of Clinical Pharmacology, Oct. 3, 2013, doi:10.1002/jcph.194. [Epub ahead of print].
Matz et al., "Micellar Complexes of Human Apolipoprotein A-I with Phosphatidylcholines and Cholesterol Prepared from Cholate-Lipid Dispersions," The Journal of Biological Chemistry, vol. 257, No. 8, pp. 4535-4540, Apr. 25, 1982.
Diditchnko et al., "Novel Formulation of a Reconstituted High-Density Lipoprotein (CSL112) Dramatically Enhances ABSA!-Dependent Cholesterol Efflux," Arterioscler. Thromb. Vasc Biol, vol. 33, pp. 1-10, Sep. 2013.

* cited by examiner

*Primary Examiner* — Christina Bradley
(74) *Attorney, Agent, or Firm* — Foley & Lardner LLP

(57) ABSTRACT

A reconstituted high density lipoprotein formulation having relatively low toxicity comprises an apolipoprotein such as ApoAI or fragment thereof, a lipid and a detergent at a level which is about 5-50% of that which would normally cause liver toxicity upon administration to a human. The lipid is optimally phosphatidylcholine at about 30-50 g/L and the molar ratio of apolipoprotein:lipid is optimally in the range 1:40 to 1:75. The formulation is useful for treating diseases or conditions such as cardiovascular disease, hypercholesterolaemia and hypocholesterolaemia inclusive of acute coronary syndrome (ACS), atherosclerosis and myocardial infarction.

11 Claims, 9 Drawing Sheets

RECONSTITUTED HIGH DENSITY LIPOPROTEIN FORMULATION AND PRODUCTION METHOD THEREOF

TECHNICAL FIELD

THIS INVENTION relates to reconstituted high density lipoprotein formulations. More particularly, this invention relates to reconstituted high density lipoprotein formulations having reduced toxicity.

BACKGROUND

High density lipoprotein (HDL) is a class of heterogeneous lipoproteins containing lipid and protein characterized by high density (>1.063 g/mL) and small size (Stoke's diameter=5 to 17 nm). The various HDL subclasses vary in quantitative and qualitative content of lipids, apolipoproteins, enzymes, and lipid transfer proteins, resulting in differences in shape, density, size, charge, and antigenicity. Apolipoprotein A-I (Apo-AI) is the predominant HDL protein, although other apolipoproteins such as Apo-AII and Apo-V may be present.

Epidemiological and clinical studies have established an inverse association between levels of high-density lipoprotein cholesterol (HDL-C) and risk of cardiovascular disease (reviewed in Assmann et al., 2004, Circulation 109 III-8). More particularly, clinical administration of reconstituted HDL formulations has been shown to confer beneficial effects to hypercholesterolemic patients suffering from recent acute coronary syndromes (ACS).

Typically, such reconstituted HDL formulations comprise a protein such as Apo-AI, a lipid such as phosphatidylcholine and a detergent such as cholate or deoxycholate. In addition, cholesterol may be included. As discussed in U.S. Pat. No. 5,652,339, it may be advantageous to produce reconstituted HDL formulations without using organic solvents, which in some cases are used for dissolving the lipid component (e.g. phosphatidylcholine) when producing the reconstituted HDL formulation. A reconstituted HDL formulation of this type, designated CSL-111, was clinically trialled but the higher dosage treatment was discontinued early following liver function test abnormalities. Patients treated with CSL111 showed beneficial trends in indices of plaque burden. However, statistical significance was not obtained in percentage change in atheroma volume or nominal change in plaque volume when compared with placebo (Tardif et al., 2007, JAMA-Exp. 297 E1).

SUMMARY

It is an object of the invention to provide a reconstituted HDL formulation which alleviates or avoids one or more of the deficiencies of prior art reconstituted HDL formulations.

It is a preferred object of the invention to provide a reconstituted HDL formulation with reduced or minimal toxicity.

It is another preferred object of the invention to provide a reconstituted HDL formulation that is efficacious in the prophylactic and/or therapeutic treatment of diseases or conditions including, but not limited to, coronary atherosclerosis.

The invention is broadly directed to a lipoprotein formulation which comprises an apolipoprotein, a phospholipid and a detergent at a level which is not toxic, or at least displays relatively low toxicity. In particular embodiments, the level of detergent and lipid is at a level less than that which causes, results in or is associated with liver toxicity.

In one aspect, the invention provides a reconstituted high density lipoprotein (rHDL) formulation comprising an apolipoprotein or fragment thereof; a lipid; and a detergent at a level which is about 5-50% of that present in an rHDL formulation that displays liver toxicity upon administration to a human.

In another aspect, the invention provides a method of producing a rHDL formulation comprising an apolipoprotein; a lipid; and a detergent, said method including the step of providing said detergent at a level which is about 5-50% of that present in an rHDL formulation that displays liver toxicity upon administration to a human.

In yet another aspect, the invention provides a method of treating a disease, disorder or condition in a human including the step of administering to the human an rHDL according to the first aspect or produced according to the method of the second aspect, to thereby treat said disease, disorder or condition in the human.

In still yet another aspect the invention provides an rHDL formulation according to the first aspect or produced according to the method of the second aspect, for use in treating a disease, disorder or condition in a human.

Preferably, the level of detergent is about 5-10% of that which displays liver toxicity. In certain embodiments this is equivalent to about 0.03 g/g apolipoprotein.

Preferably, the detergent is a bile salt or bile acid. More preferably, the detergent is sodium cholate.

The apolipoprotein may be any apolipoprotein which is a normal and/or functional constituent of high density lipoprotein (HDL). The apolipoprotein is preferably at a concentration of about 20-50 g/L. Preferably, the apolipoprotein is Apo-A1 or a fragment thereof.

Suitably, the level of lipid is about 20-70% of that which causes, or is associated with, liver toxicity. Preferably, the lipid is at a concentration of about 30-60 g/L. A particularly advantageous concentration of lipid is about 30-50 g/L, or in certain embodiments about 34 or 47 g/L.

Preferably, the lipid is a phospholipid. More preferably the phospholipid is, or comprises, phosphatidylcholine (PC).

In one preferred embodiment, the molar ratio of apolipoprotein:lipid is in the range 1:20 to 1:100. More preferably, the molar ratio of apolipoprotein:lipid is in the range of 1:40 to 1:75. A particularly advantageous ratio of apolipoprotein:lipid is about 1:40 or 1:55.

Suitably, the rHDL formulation further comprises a stabilizer. Preferably, the stabilizer is a sugar such as sucrose. A preferred concentration is about 65-85 g/L rHDL formulation.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF THE FIGURES

Reference is made to the following Figures which assist in understanding non-limiting embodiments of the invention described in detail hereinafter wherein.

DETAILED DESCRIPTION

Figure 1:
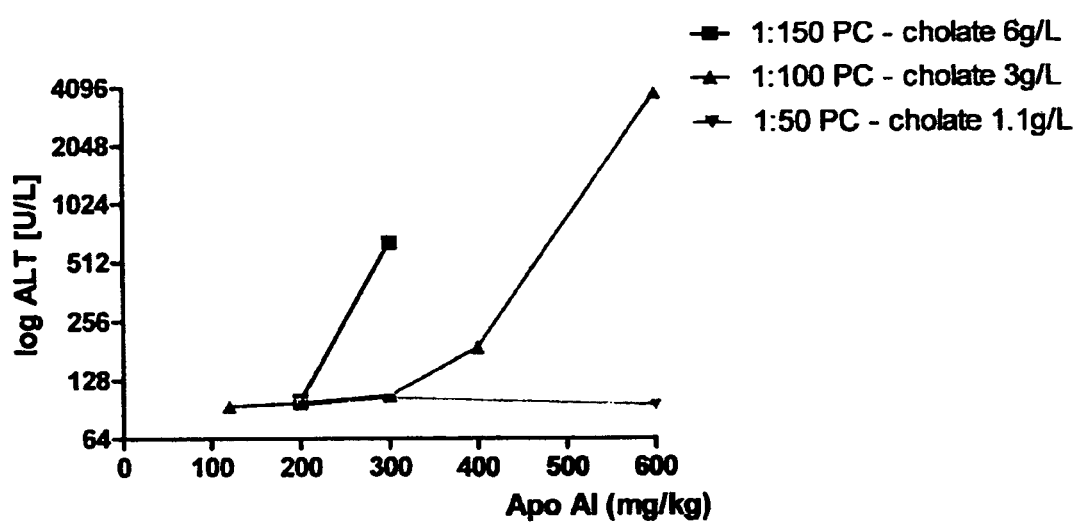
FIG. 1 shows results of acute rat studies indicating that simultaneous reduction of both cholate and phosphatidylcholine reduce liver toxicity.

The invention at least partly arises from the unexpected discovery that the liver toxicity displayed by the CSL111 reconstituted HDL (rHDL) formulation described in the prior art was due to excess detergent, particularly when considered in terms of the ratio of detergent to Apo-A1 in the formulation. In this regard, the level of sodium cholate was about 0.3 g/g Apo-A1. However, the inventors have also discovered that detergent cannot be totally eliminated and must be retained at a level whereby the rHDL formulation displays sufficient stability and therapeutic activity.

Furthermore, a reduction in the concentration of lipid compared to that present in CSL111 has been unexpectedly found to reduce liver toxicity without substantially compromising the therapeutic activity of the rHDL formulation.

In a yet further discovery, a molar ratio of apolipoprotein:lipid has been identified which is optimal for the rHDL formulation.

Accordingly, in one aspect the present invention provides an rHDL formulation comprising an apolipoprotein or fragment thereof; a lipid and a level of detergent which is about 5-50% of that present in a rHDL formulation that would display liver toxicity upon administration to a human.

As used herein, a "reconstituted HDL (rHDL)" formulation may be any artificially-produced lipoprotein formulation or composition that is functionally similar to, analogous to, corresponds to, or mimics, high density lipoprotein (HDL) typically present in blood plasma. rHDL formulations includes within their scope "HDL mimetics" and "synthetic HDL particles".

In this context, by "displays liver toxicity upon administration of the rHDL formulation to a human" means a level of detergent in an rHDL formulation which following administration to a human causes, results in, or is at least associated with an adverse event thereafter. Typically, the adverse event is liver toxicity, such as evidenced by abnormal or compromised liver function. Non-limiting examples of liver function(s) that may be abnormal or compromised include elevated alanine aminotransferase activity (ALT), elevated aspartate aminotransferase (AST) activity and/or elevated bilirubin levels. According to the invention, a suitable level of detergent is that which does not cause, result in, or is not associated with an adverse event, as hereinbefore described. Typically, this would be measured at the end of infusion.

Preferably, the level of detergent is about 5-35% of that which displays liver toxicity. This range includes, for example, 5%, 10%, 15%, 20%, 25%, 30% and 35%. More preferably, the level of detergent is about 5-20% of that which displays liver toxicity. Advantageously, the level is about 5-10% of that which displays liver toxicity. Preferably, these levels are expressed in terms of the minimum or threshold level of detergent that displays liver toxicity.

By way of example, a level of detergent which has been shown in work leading to the present invention to cause, result in or at least be associated with liver toxicity is 0.3 g/g Apo-AI or 6 g/L rHDL formulation (at 20 g/L Apo-AI). Accordingly, 5-10% of this level of detergent is 0.015-0.03 g/g Apo-AI or 0.5-0.9 g/L rHDL formulation (at 30 g/L Apo-AI).

The "level" of detergent may be an absolute amount of detergent, a concentration of detergent (e.g mass per unit volume of rHDL formulation) and/or a ratio of the amount or concentration of detergent relative to another amount or concentration of a component of the rHDL formulation. By way of example only, the level of detergent may be expressed in terms of the total mass of apolipoprotein (e.g. Apo-AI) present in the rHDL formulation.

While safety and avoidance of liver toxicity is one object of the invention, the invention also requires a level of detergent sufficient to maintain rHDL formulation stability. As will be described in more detail in the Examples, a detergent concentration no less than about 0.45 g/L of rHDL formulation with 30 g/L apolipoprotein is optimal in terms of both stability and non-toxicity. Stability may advantageously be measured by any means known in the art, although turbidity of the rHDL formulation is a preferred measure.

The detergent may be any ionic (e.g cationic, anionic, Zwitterionic) detergent or non-ionic detergent, inclusive of bile acids and salts thereof, suitable for use in rHDL formulations. Ionic detergents may include bile acids and salts thereof, polysorbates (e.g PS80), CHAPS, CHAPSO, cetyl trimethyl-ammonium bromide, lauroylsarcosine, tert-octyl phenyl propanesulfonic acid and 4'-amino-7-benzamido-taurocholic acid.

Bile acids are typically dihydroxylated or trihydroxylated steroids with 24 carbons, including cholic acid, deoxycholic acid chenodeoxycholic acid or ursodeoxycholic acid. Preferably, the detergent is a bile salt such as a cholate, deoxycholate, chenodeoxycholate or ursodeoxycholate salt. A particularly preferred detergent is sodium cholate.

The apolipoprotein may be any apolipoprotein which is a functional, biologically active component of naturally-occurring HDL or of a reconstituted high density lipoprotein (rHDL). Typically, the apolipoprotein is either a plasma-derived or recombinant apolipoprotein such as Apo-AI, Apo-AII or Apo-AV, pro-apo-A1 or a variant such as Apo-AI Milano. Preferably, the apolipoprotein is Apo-AI. Also contemplated are biologically-active fragments of the apolipoprotein. Fragments may be naturally occurring, chemical synthetic or recombinant. By way of example only, a biologically-active fragment of Apo-AI preferably has at least 50%, 60%, 70%, 80%, 90% or 95-100% or even greater than 100% of the lecithin-cholesterol acyltransferase (LCAT) stimulatory activity of Apo-AI.

Suitably, the apolipoprotein is at a concentration of about 20-50 g/L. This includes 20, 25, 30, 35, 40, 45 and 50 g/L and any ranges between these amounts. The apolipoprotein is preferably at a concentration of about 30 g/L.

The rHDL formulation comprises a lipid at a level which does not cause liver toxicity. Suitably, the level of lipid is about 20-70% of that which causes, or is associated with, liver toxicity. In particular embodiments, the level of lipid is preferably about 25%, 30%, 35%, 40%, 45%, 50%, 55%, 60% or 65% of that which causes, or is associated with, liver toxicity, and any ranges between these amounts. Preferably, these levels are expressed in terms of the minimum or threshold level of lipid that displays liver toxicity.

By way of example, a level of lipid which has been shown in work leading to the present invention to cause, result in or at least be associated with liver toxicity is 84 g/L. Accordingly, the lipid is preferably at a concentration of about 30-60 g/L. This includes 30, 35, 40, 45, 50, 55 and 60 g/L and any ranges between these amounts. A particularly advantageous concentration of lipid is about 30-50 g/L, or in certain embodiments about 34 or 47 g/L.

The "level" of lipid may be an absolute amount of lipid, a concentration of lipid (e.g. mass per unit volume of rHDL formulation) and/or a ratio of the amount or concentration of lipid relative to another amount or concentration of a component of the rHDL formulation. By way of example only, the level of lipid may be expressed in terms of a molar ratio of apolipoprotein (e.g. Apo-AI) present in the rHDL formulation.

In one preferred embodiment, the molar ratio of apolipoprotein:lipid is in the range 1:20 to 1:100. This range includes molar ratios such as 1:30, 1:40, 1:50, 1:60, 1:70, 1:80 and 1:90. More preferably, the molar ratio of apolipoprotein:lipid is in the range of 1:40 to 1:75. A particularly advantageous ratio of apolipoprotein:lipid is about 1:40 or 1:55.

The lipid may be any lipid which is a functional, biologically active component of naturally-occurring HDL or of reconstituted high density lipoprotein (rHDL). Such lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), phosphatidic acid, phosphatidylethanolamine (PE) (cephalin), phosphatidylglycerol (PG), phosphatidylserine (PS), phosphatidylinositol (PI) and sphingomyelin (SM) or natural or synthetic derivatives thereof. Natural derivatives include egg PC, egg PG, soy bean PC, hydrogenated soy bean PC, soy bean PG, brain PS, sphingolipids, brain SM, galactocerebroside, gangliosides, cerebrosides, cephalin, cardiolipin, and dicetylphosphate. Synthetic derivatives include dipahnitoylphosphatidylcholine (DPPC), didecanoylphosphatidylcholine (DDPC), dierucoylphosphatidylcholine (DEPC), dimyristoylphosphatidylcholine (DMPC), distearoylphosphatidylcholine (DSPC), dilaurylphosphatidylcholine (DLPC), palmitoyloleoylphosphatidylcholine (POPC), palmitoylmyristoylphosphatidylcholine (PMPC), palmitoylstearoylphosphatidylcholine (PSPC), dioleoylphosphatidylcholine (DOPC), dioleoylphosphatidylethanolamine (DOPE), dilauroylphosphatidylglycerol (DLPG), distearoylphosphatidylglycerol (DSPG), dimyristoylphosphatidylglycerol (DMPG), dipalmitoylphosphatidylglycerol (DPPG), distearoylphosphatidylglycerol (DSPG), dioleoylphosphatidylglycerol (DOPG), palmitoyloleoylphosphatidylglycerol (POPG), dimyristoylphosphatidic acid (DMPA), dipalmitoylphosphatidic acid (DPPA), distearoylphosphatidic acid (DSPA), dimyristoylphosphatidylethanolamine (DMPE), dipalmitoylphosphatidylethanolamine (DPPE), dimyristoylphosphatidylserine (DMPS), dipalmitoylphosphatidylserine (DPPS), distearoylphosphatidylethanolamine (DSPE), dioleoylphosphatidylethanolamine (DOPE) dioleoylphosphatidylserine (DOPS), dipalmitoylsphingomyelin (DPSM) and distearoylsphingomyelin (DSSM). The phospholipid can also be a derivative or analogue of any of the above phospholipids.

Preferably the phospholipid is, or comprises, phosphatidylcholine, alone or in combination with one or more other phospholipids. An example of another phospholipid is sphingomyelin.

Suitably, the rHDL formulation further comprises a stabilizer. In particular, the stabilizer maintains stability of the rHDL formulation during lyophilisation. Suitably the stabilizer is a carbohydrate such as a sugar or sugar alcohol. Examples of suitable sugar alcohols are mannitol and sorbitol. Preferably, the stabilizer is a disaccharide sugar such as sucrose. A preferred concentration of sucrose is about 65-85 g/L (equivalent to about 6.5-8.5% w/v) of rHDL formulation.

Preferably, the concentration of sucrose is about 75 g/L (equivalent to about 7.5% w/w). This is a reduced sucrose concentration, both in absolute terms and relative to the lipoprotein concentration, compared to CSL111. It is proposed that this relatively reduced sucrose may allow for a faster infusion rate of the rHDL formulation of the invention. Other stabilizers may be or include amino acids (e.g. glycine, proline), antioxidants, emulsifiers, surfactants, chelating agents, gelatine, synthetic oils, polyols, alginate or any pharmaceutically acceptable carriers and/or excipients, although without limitation thereto. In this regard, reference is made by way of example to "Pharmaceutical Formulation Development of Peptides and Proteins", Frokjaer et al., Taylor &; Francis (2000), "Handbook of Pharmaceutical Excipients", 3rd edition, Kibbe et al., Pharmaceutical Press (2000) and International Publication WO2009/025754.

In a particularly preferred embodiment; the rHDL formulation comprises:
(i) about 30 g/L Apo-AI;
(ii) about 0.03 g sodium cholate per gram Apo-AI;
(iii) about 34 or 47 g/L phosphatidylcholine; and
(iv) about 75 g/L sucrose;
wherein the molar ratio of Apo-AI:phosphatidylcholine is about 1:40 or 1:55.

In another aspect, the invention provides a method of producing a rHDL formulation comprising an apolipoprotein; a lipid; and a detergent, said method including the step of providing said detergent at a level which is about 5-50% of that present in an rHDL formulation that displays liver toxicity upon administration to a human.

Preferably, said method includes the step of providing said detergent at a level which is about 5-10% of that which displays liver toxicity upon administration to a human.

In a preferred embodiment of the method, an initial or starting level of detergent is reduced or removed to a level which does not display liver toxicity upon administration of the rHDL formulation to a human.

Reduction or removal of detergent may be performed by any means known in the art including filtration, hydrophobic adsorption or hydrophobic interaction chromatography, dialysis, ion-exchange adsorption and ion-exchange chromatography, for example.

In some embodiments, non-polar polystyrene resins may be suitable for reducing detergent levels. Such resins preferably are in the form of a cross-linked copolymer (e.g. a cross-linked styrene and divinylbenzene copolymer). Non-limiting examples include Amberlite XAD-2 and Bio Beads SM.

Filtration includes gel filtration, gel permeation, diafiltration and ultrafiltration, although without limitation thereto, as are well understood in the art. A non-limiting example of gel permeation may utilize porous, cross-linked dextran such as Sephadex resins.

In a particularly preferred embodiment particularly suitable for large scale manufacture, the detergent level is reduced by diafiltration.

Suitably, the method includes the step of combining the lipid and the apolipoprotein in the absence of organic solvent.

Accordingly, in one preferred embodiment the invention provides a method of producing a rHDL formulation including the steps of:
(I) adding phosphatidylcholine without organic solvent and a cholate detergent to an Apo-A1 solution;
(II) reducing the level of cholate detergent in the solution produced at step (I) to about 0.03 g/g Apo-A1;
(III) adding a stabilizer, preferably sucrose, to the solution at step (II).

Preferably, at step (I), phosphatidylcholine is added so that the Apo-AI:phosphatidylcholine ratio is about 1:40 or 1:55.

Preferably, the final concentration of sucrose at step (III) is about 75 g/L.

Suitably, the method further includes the step (IV) of lyophilizing the rHDL formulation produced at step (III).

Figure 9:
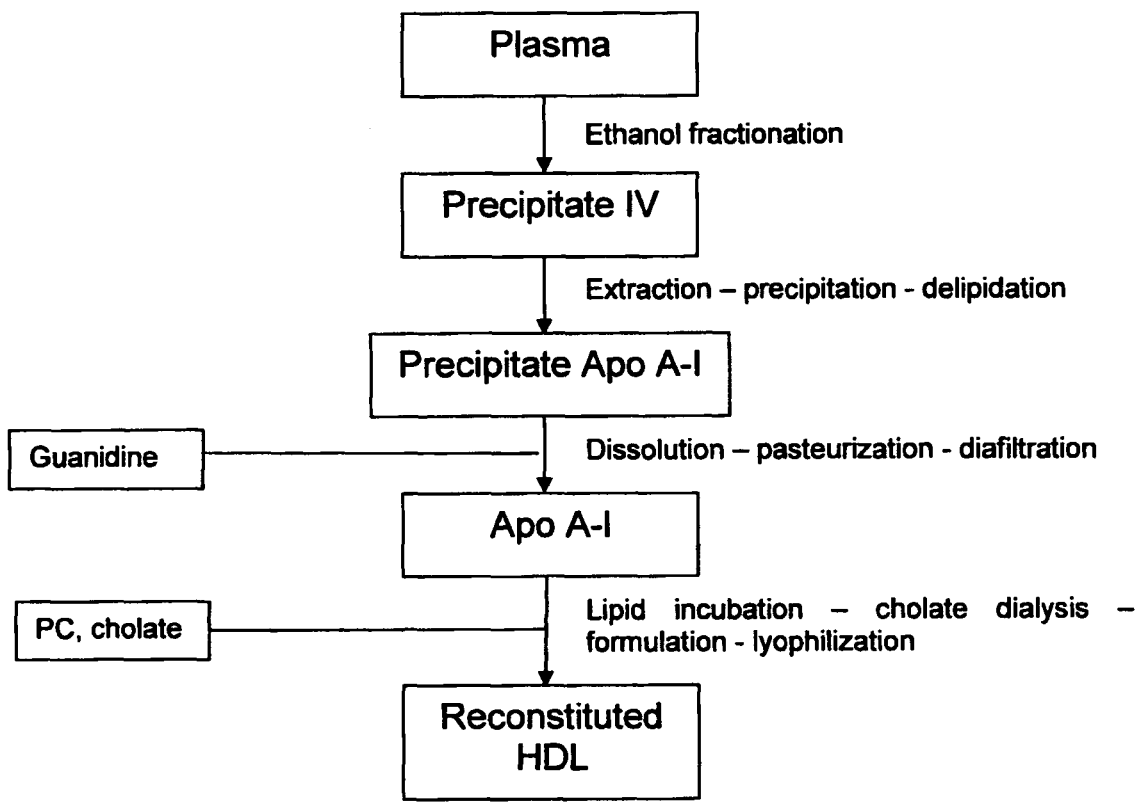
FIG. 9 provides an overview of an embodiment of an rHDL formulation manufacturing process.

It will be appreciated that in a particular embodiment the method of producing a rHDL formulation is suitable for large scale, commercial manufacturing of a rHDL formulation of a quality and safety suitable for administration to humans. A non-limiting example of a large scale, commercial manufacturing process is summarized in FIG. 9.

In yet another aspect, the invention provides a method of treating a disease, disorder or condition in a human including the step of administering to the human a rHDL as hereinbefore described or produced according to the method as hereinbefore described, to thereby treat said disease, disorder or condition in the human.

The invention also provides an rHDL formulation as hereinbefore described or produced according to the method as hereinbefore described, for use in treating a disease, disorder or condition in a human.

Suitably, the disease, disorder or condition is responsive to prophylactic or therapeutic administration of said rHDL formulation. Non-limiting examples of such diseases, disorders or conditions include cardiovascular disease (e.g acute coronary syndrome (ACS, atherosclerosis and myocardial infarction) or diseases, disorders or conditions such as diabetes, stroke or myocardial infarction that predispose to ACS, hypercholesterolaemia (e.g elevated serum cholesterol or elevated LDL cholesterol) and hypocholesterolaemia resulting from reduced levels of high-density lipoprotein (HDL), such as is symptomatic of Tangier disease.

rHDL formulations may be administered by any route of administration known in the art. Typically, rHDL formulations are administered parenterally, such as by intravenous infusion or injection.

The administered dosage of the rHDL formulation may be in the range 1-120 mg/kg body weight. Preferably, the dosage is in the range 5-80 mg/kg inclusive of 10 mg/kg, 20 mg/kg, 30 mg/kg, 40 mg/kg, 50 mg/kg, 60 mg/kg and 70 mg/kg dosages.

So that preferred embodiments of the invention may be fully understood and put into practical effect, reference is made to the following non-limiting Examples.

EXAMPLES

The Examples provided hereinafter describe initial studies to determine which factors of rHDL formulations (such as CSL111) contribute to liver toxicity (Examples 1 & 2) and development and toxicity testing of embodiments of a rHDL formulation of the invention (Examples 3 to 8).

Example 1

Liver Toxicity Study Comparing Different Apo-A1:PC Ratios and the Effect of Controlling Cholate Levels The level of liver toxicity as measured by ALT activity was determined in the rat model (see details of model below in Example 2) for HDL preparations containing different Apo AI:PC ratio's (1:150, 1:100 & 1:50). Each HDL preparation contained different cholate concentrations with levels ranging from 6 g/L for 1:150 to 1.1 g/L for the 1:50 preparation.

Figure 2:
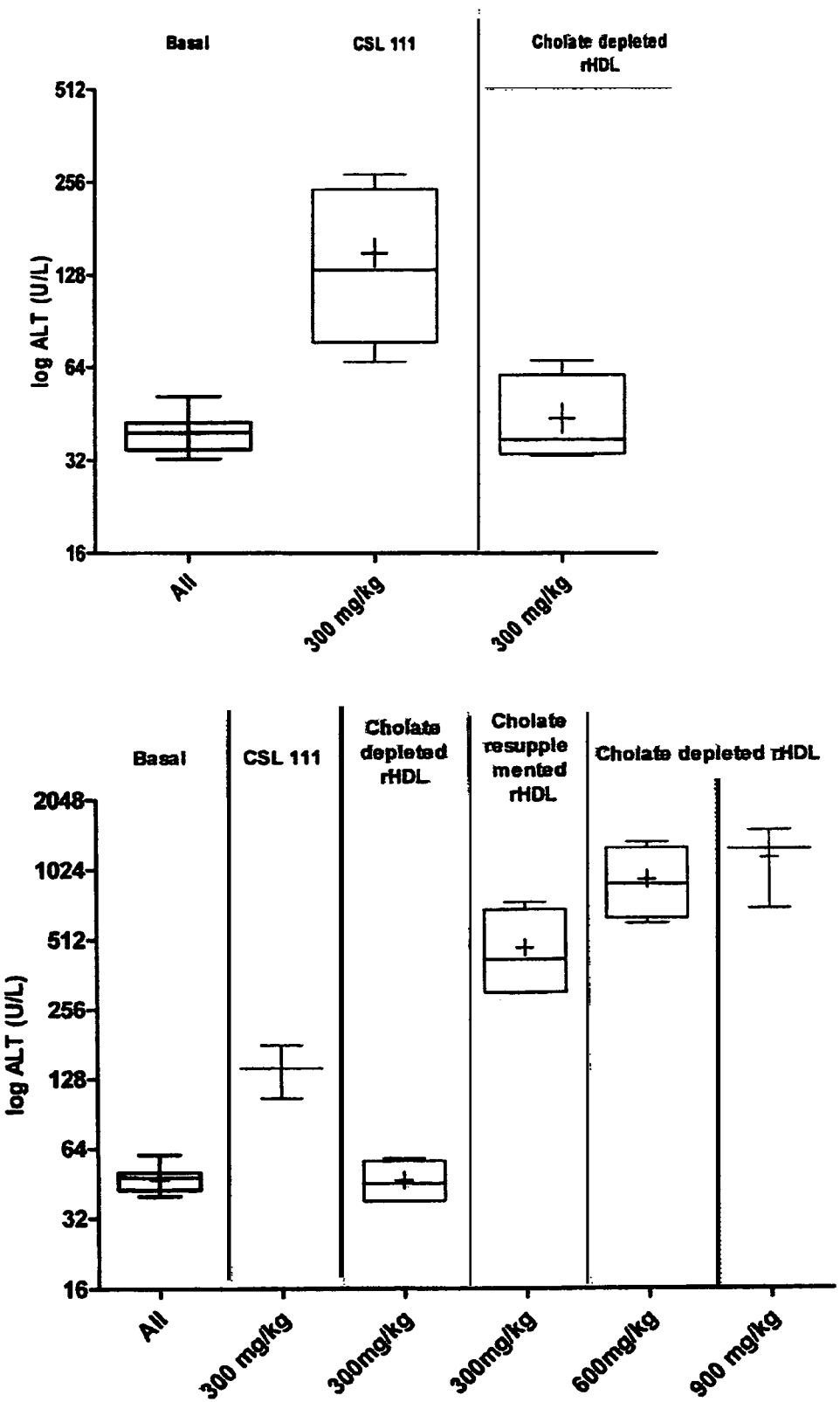
FIG. 2 shows results of acute rat studies indicating that selective reduction of cholate reduces liver toxicity.

The results indicated that increased ALT levels were observed for the 1:150 HDL preparation for doses from 300 mg/kg. The 1:100 HDL preparation caused increased ALT levels at dosages from 400 mg/kg, with levels increasing considerably at 600 mg/kg. In contrast an increase in ALT activity was not observed for the 1:50 HDL preparation up to a 600 mg/kg dose (FIG. 1). These results suggest the liver toxicity is reduced by either the level of PC and/or the level of cholate in the HDL preparation. To investigate whether the level of cholate had a direct affect on ALT activity a further study was conducted in which CSL111 was depleted of cholate. The results demonstrate that the reduction in cholate in a CSL111 preparation resulted in a reduction of ALT levels when infused to a rat at 300 mg/kg (FIG. 2). Further if the cholate was then added back to the depleted HDL preparation the resupplemented HDL preparation caused increased ALT levels when infused into a rat at 300 mg/kg (FIG. 2). These studies demonstrate that reducing cholate to about 1 g/L substantially reduces rHDL toxicity, but also an additional contributing factor is a reduction in PC to a ratio of about 1:50 apoA1:PC.

Example 2

Liver Toxicity Study Comparing Graded Cholate Levels and Apo-A1:PC Ratios

Introduction

The goal of this study was to determine the hepatotoxicity of reconstituted HDL formulations (rHDL) with graded cholate concentrations and Apo A-I to PC ratios as follows rHDL PC 1:150 (3 g/L Cholate), rHDL PC 1:100 (1 g/L Cholate), rHDL PC 1:50 (3 g/L Cholate), rHDL PC 1:50 (0.2 g/L Cholate). The conscious rat model was used to determine the effect of the aforementioned formulations on liver function. Hepatotoxicity was evaluated by determination of liver enzyme activity (ALT and AST) in serum.

Apo-A1 is considered to be the active component of the formulations and plasma levels of Apo-A1 are the key indicator of exposure.

Materials and Methods

Administration of Test rHDL Formulations

Test rHDL Formulation 1
Substance/INN: rHDL PC 1:150 (3 g/L Cholate)
Manufacturer: CSL Behring AG, Bern, Switzerland
Lot number: Q.3
Dose: 600 mg/kg b.w.
Route: iv. infusion via tail vein
Frequency: infusion t=0-60 min.
Application volume: 31.25 mL/kg/h Test rHDL Formulation 2
Substance/INN: rHDL PC 1:100 (1 g/L Cholate)
Manufacturer: CSL Behring AG, Bern, Switzerland
Lot number: O.3-2
Dose: 600 mg/kg b.w.
Route: i.v. infusion via tail vein
Frequency: infusion t=0-60 min.
Application volume: 30.30 ml/kg/h Test rHDL Formulation 3
Substance/INN: rHDL PC 1:50 (3 g/L Cholate)
Manufacturer: CSL Behring AG, Bern, Switzerland
Lot number: P.3
Dose: 600 mg/kg b.w.
Route: i.v. infusion via tail vein
Frequency: infusion t=0-60 min.
Application volume: 31.58 ml/kg/h
Expiry date: n.a.

Test rHDL Formulation 4
Substance/INN: rHDL PC 1:50 (0.2 g/L Cholate)
Manufacturer: CSL Behring AG, Bern, Switzerland Lot number: P.2
Dose: 900 mg/kg b.w.
Route: i.v. infusion via tail vein
Frequency: infusion t=0-120 min.
Application volume: 23.08 ml/kg/h b.w.
Study Design This study was designed as an open four-armed trial in a total of 14 rats. The dosing regimen is summarized in Table 1.
Treatment Groups

TABLE 1

Treatment groups

| No. | Treatment | Dose (mg/kg) | Route | volume (mL/kg/h) | schedule (t = x min) | N |
|---|---|---|---|---|---|---|
| 1 | rHDL PC 1:150 (3 g/L Cholate) | 600 | i.v. | 31.25 | 0-60 | 4 |
| 2 | rHDL PC 1:100 (1 g/L Cholate) | 600 | i.v. | 30.30 | 0-60 | 4 |
| 3 | rHDL PC 1:50 (3 g/L Cholate) | 600 | i.v. | 31.58 | 0-60 | 4 |
| 4 | rHDL PC 1:50 (0.2 g/L Cholate) | 900 | i.v. | 23.08 | 0-120 | 2 |

Experimental Animals
Species: Rats
Strain: CD
Sex: male
No. of animals: 14
Supply: Charles River Laboratories (Sulzfeld, Germany)
Body weight: 286-328 g
Age at arrival: 7-9 weeks
Housing: macrolon cages
Bedding: wood shavings (Braun, Battenberg, Germany)
Water: tap water, ad libitum
Food: standard rat diet (Ssniff-Versuchsdiäten, Soest, Germany)
Light/darkness: 12 h/12 h
Temperature: 21-22° C.
Relative humidity: 40-50%

Animals were placed in restraint devices (rat holder) and the lateral tail vein was punctured with an i.v. catheter. Test articles were infused for 60/120 minutes.

Blood samples were withdrawn from the retro-orbital venous complex and collected into serum tubes at baseline, 1 h/2 h and 7 h/8 h following i.v. infusion. Blood samples were processed to serum, stored at −20° C.
Determination of Liver Enzymes The samples were analyzed for AST and ALT activity using enzymatic photometric test kits available commercially (Greiner Biochemica).
Determination of Apo A-I Plasma Level The determination of human Apo A-I levels was performed by a nephelometric assay.
Results Under investigation were rHDL formulations with Apo A-I to PC ratios of 1:50, 1:100 and 1:150 as well as a defined Cholate concentrations of 1 or 3 g/L or Cholate depleted (0.2 g/L). Saline served as vehicle and CSL 111 as positive control. Blood sampling was taken at baseline (time point 0) at the infusion end (1 h or 2 h, 600 and 900 mg/kg, respectively), and at 7 h or 8 h. The liver enzymes activity (ALT and AST) and human Apo A-I levels were estimated at the aforementioned time-points.

The AST concentration at baseline ranged between 63 and 87 U/L. The AST concentration increased at the end of infusion and at the 7 h/8 h time-point for all formulations excep Apo AI:PC 1:50 (Cholate 0.2 g/L).

The ALT concentration at baseline ranged between 39 and 45 U/L. The AST concentration increased at the end of infusion and at time-point 7 h/8 h for all formulations except Apo AI:PC 1:50 (Cholate 0.2 g/L).

The human Apo A-I concentration at baseline was below the lowest limit of detection. At the end of infusion the concentration increased to approximately 13 g/L for all formulations dosed at 600 mg/kg. The formulation 1:50 at 900 mg/kg resulted in an Apo A-I concentration of 15 g/L.

The means and standard deviations for all groups, doses and time-points are given in Tables 2 to 4.

TABLE 2

AST serum levels (mean ± SD)
Treatment/Serum concentration (U/L)

| Time-point | rHDL PC 1:150 (3 g/L Cholate) 600 mg/kg n = 4 | rHDL PC 1:100 (1 g/L Cholate) 600 mg/kg n = 4 | rHDL PC 1:50 (3 g/L Cholate) 600 mg/kg n = 4 | rHDL PC 1:50 (0.2 g/L Cholate) (*) 900 mg/kg n = 2 |
|---|---|---|---|---|
| Baseline | 65.81 ± 15.96 | 63.33 ± 7.16 | 66.83 ± 9.62 | 87.26 ± 25.41 |
| 1 h/2 h(*) | 275.48 ± 66.20 | 166.19 ± 118.42 | 287.77 ± 122.04 | 55.29 ± 1.71 |
| 7 h/8 h(*) | 1755.65 ± 562.36 | 433.42 ± 320.17 | 286.57 ± 65.38 | 91.44 ± 15.45 |

TABLE 3

ALT serum levels after (mean ± SD)
Treatment/Serum concentration (U/L)

| Time-point | rHDL PC 1:150 (3 g/L Cholate) 600 mg/kg n = 4 | rHDL PC 1:100 (1 g/L Cholate) 600 mg/kg n = 4 | rHDL PC 1:50 (3 g/L Cholate) 600 mg/kg n = 4 | rHDL PC 1:50 (0.2 g/L Cholate) (*) 900 mg/kg n = 2 |
|---|---|---|---|---|
| Baseline | 38.91 ± 3.28 | 43.02 ± 6.39 | 45.27 ± 4.07 | 41.51 ± 6.87 |
| 1 h/2 h(*) | 211.80 ± 61.26 | 105.19 ± 69.09 | 147.62 ± 51.32 | 33.11 ± 2.98 |
| 7 h/8 h(*) | 1552.96 ± 715.45 | 435.66 ± 323.69 | 263.07 ± 69.86 | 55.90 ± 16.92 |

TABLE 4

| | Apo A-I serum levels (mean ± SD) Treatment/Serum concentration (g/L) | | | |
|---|---|---|---|---|
| Time-point | rHDL PC 1:150 (3 g/L Cholate) 600 mg/kg n = 4 | rHDL PC 1:100 (1 g/L Cholate) 600 mg/kg n = 4 | rHDL PC 1:50 (3 g/L Cholate) 600 mg/kg n = 4 | rHDL PC 1:50 (0.2 g/L Cholate) (*) 900 mg/kg n = 2 |
| Baseline | 0.246 ± 0.000 | 0.246 ± 0.000 | 0.246 ± 0.000 | 0.246 ± 0.000 |
| 1 h/2 h(*) | 13.150 ± 0.687 | 13.900 ± 0.248 | 13.000 ± 1.217 | 14.700 ± 1.414 |
| 7 h/8 h(*) | 10.175 ± 0.185 | 7.700 ± 1.352 | 7.075 ± 0.595 | 9.250 ± 0.283 |

Conclusion

In conclusion only the rHDL formulation Apo AI:PC ratio 1:50 (0.2 g/L cholate) at 900 mg/kg induced no liver function test abnormalities. In contrast the same 1:50 rHDL formulation with higher cholate levels (3 g/L) at 600 mg/kg showed elevated levels of both AST and ALT. This suggests that liver toxicity is best minimized by controlling the lipid and residual detergent content of the rHDL formulations.

Example 3

Stability Trials Comparing Cholate Levels in rHDL Formulations

An embodiment of an rHDL formulation of the invention displays significantly reduced liver toxicity compared to prior art rHDL formulation CSL111, while maintaining a biological activity at least equivalent to CSL111. This rHDL formulation distinguishes from CSL111 by a lower protein to PC ratio, a lower level of cholate, a higher protein content and a reduced sucrose concentration.

Formulation of Reconstituted HDL
Starting Material Apo-AI

As starting material a purified and pasteurized Apo-AI solution was used. The batch size was either 30 g or 35 g protein.

Lipid Solution

The formula for manufacture of the lipid solution is given below. First, the buffer solution containing 10 mM Tris, 10 mM NaCl and 1 mM EDTA was made. The required amount was calculated according to equation 1:

$$\text{amount of buffer solution [g]} = \frac{\text{amount of protein [g]} \cdot 1000 \cdot 0.025 \cdot \text{ratio}}{150} \quad \text{equation 1}$$

Next, sodium cholate (1.3 mol/mol lipid) was added to this solution and dissolved.

Then, the calculated amount of lipid was introduced (equation 2), the mixture was gently stirred for 6-18 h (lipid dissolved), and then filtered using a 0.2 μm Millipak 40 Gamma Gold, (Millipore Art. MPGL04 GH2) presterilized filter setup.

$$\text{amount of lipid [g]} = \frac{\text{amount of protein [g]} \cdot \text{ratio protein} \cdot M(\text{lipid})[\text{g/mol}] \cdot 100}{M(apoA\text{-}I)[\text{g/mol}] \cdot \text{purity lipid[\%]}} \quad \text{equation 2}$$

M(lipid): 775 g/mol for PC; 731 g/mol for SM
M(Apo-AI): 28'078 g/mol
Lipid Incubation and UF/DF The Apo-AI solution (30 g-35 g protein) was placed in a 5 L double jacket vessel and cooled to 1-4° C. Then, the lipid solution was added and stirred for 2-16 h at 1-4° C. For some experiments, the protein-lipid solution was heated for 30 min. at 30° C., cooled down and then incubated for 2-16 h at 1-4° C.

To remove the cholate, UF/DF was performed with a 10 kDa cassette against 7-9 volumes of 1% sucrose solution.

The solution was then concentrated to 22-28 g/L (20 g/L protein concentration in the FP) or 32-38 g/L (30 g/L protein concentration in the FP) and afterwards brought to 7.5% sucrose and 20 g/L or 30 g/L protein, by adding sucrose and WFI. The rHDL bulk was sterile filtered (Sartopore 2, 150 cm$^2$, PES, cut off 0.1 μm, Sartorius Art. 5441358K4-00) and filled in the laminar flow.

Reduction of Cholate with Amberlite
Preparation of Amberlite

All filtration steps were performed with a Nalgene 0.2 μm PES filter (Art. 595-4520).

Amberlite XAD-2 (400 g) was added to 500 mL methanol 20% (v/v). The suspension was stirred for 1-2 h and then the Amberlite was filtered off. Next, 300 ml 1M NaOH were placed in a 1000 mL beaker, the Amberlite added and heated to 55-60° C. under stirring for 15 minutes. The Amberlite was filtered off; afterwards this procedure was repeated another two times. Then, the Amberlite was washed with water (SWA) until pH neutral (approximately 10-15 L), filtered off, added to 300 mL methanol, stirred for 1 h and then the mixture was left at 2-8° C. at least over night. To remove the methanol, the Amberlite was filtered off, washed with approximately 10 L water (SWA) and filtered off again. Then, the Amberlite was poured into approximately a 4 L sucrose solution, either 7.5% or 10%, corresponding to the sucrose concentration of the reconstituted HDL to be depleted. The mixture was stirred for several minutes and filtered off just before using.

Reduction of Cholate with Amberlite

The reconstituted HDL was cooled to 2-8° C., the Amberlite XAD-2 was added and the mixture was stirred for 3.5 h. The Amberlite filtered off and discharged. This step was performed twice.

Depending on the experiment, for 5 g protein, 100-160 g Amberlite was used for each depleting step.

After depletion, cholate was added back to achieve the different cholate concentrations.

For the reduction of the reconstituted HDL 1:75 PC to a cholate concentration of 0.7 g/L, the amount of Amberlite to be added was experimentally determined by adding Amberlite in different ratios to the reconstituted HDL (preliminary experiment). These experiments found that one treatment with 50 g Amberlite per 5 g protein was necessary. This Amberlite to protein ratio was then used for the depletion of the main batch.

Stability Assessments
CSL111
One compound that we hypothesized may influence liver toxicity is cholate. Therefore, cholate reduction in the final formuation was a primary goal. Initial experiments were performed with CSL111. To find the minimal cholate concentration that still guarantees a stable product, reconstituted CSL111 was treated with amberlite and afterwards cholate was added back to obtain different concentrations.

Stability assessments were performed on these materials. Also, the influence of the lyophilization on the stability of CSL111 with different cholate concentrations was investigated.

Reconstituted HDL 1:50 PC/1:75 PC

Two formulations (1.50 PC and 1:75 PC) were cholate depleted with Amberlite and supplemented with cholate to obtain different cholate concentrations. These solutions were lyophilized, reconstituted and the stability investigated to determine the minimal required cholate concentration that is necessary to guarantee the stability of these formulations.

Results
Results for CSL111
The CSL111 was treated with Amberlite to remove the cholate. Cholate was then added to obtain the different concentrations required for the study.

Figure 3:
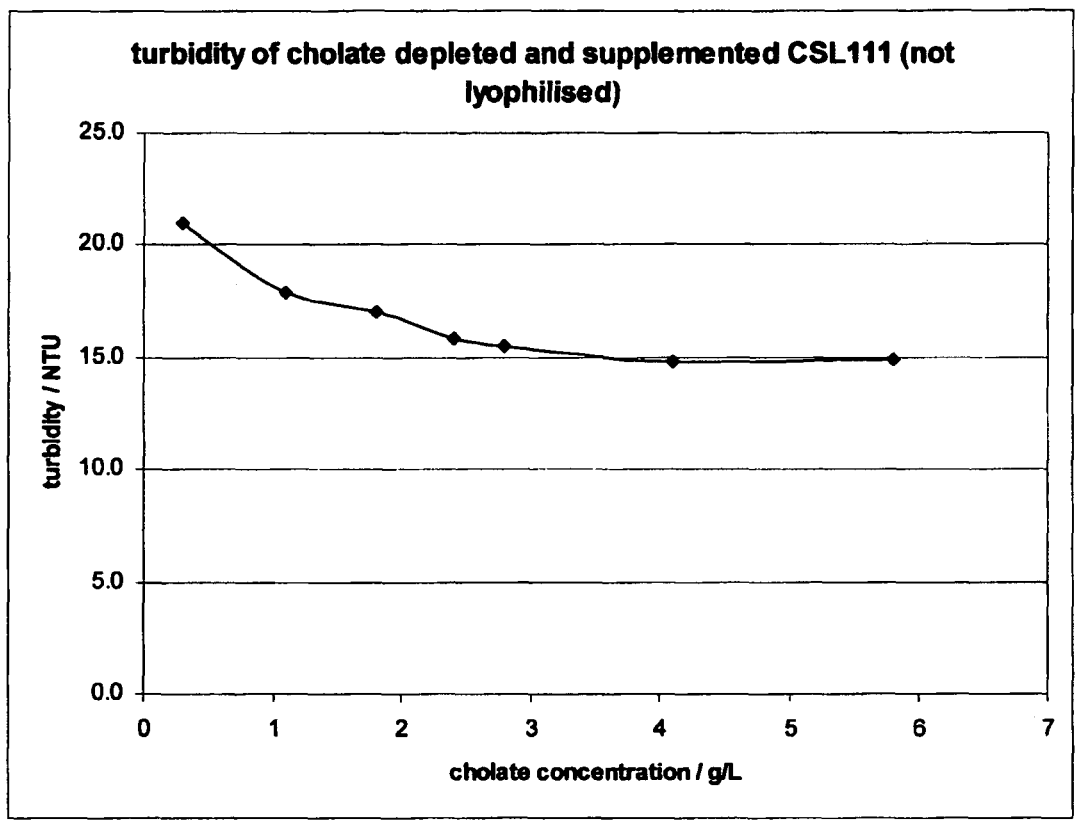
FIG. 3 shows results of turbidity analysis of CSL111 in the presence of different concentrations of cholate.

In the range below 2.8 g/L cholate, the turbidity increased as the cholate concentration was further reduced. For cholate concentrations above 2.8 g/L, almost no change of the turbidity values was detected (FIG. 3).

Figure 4:
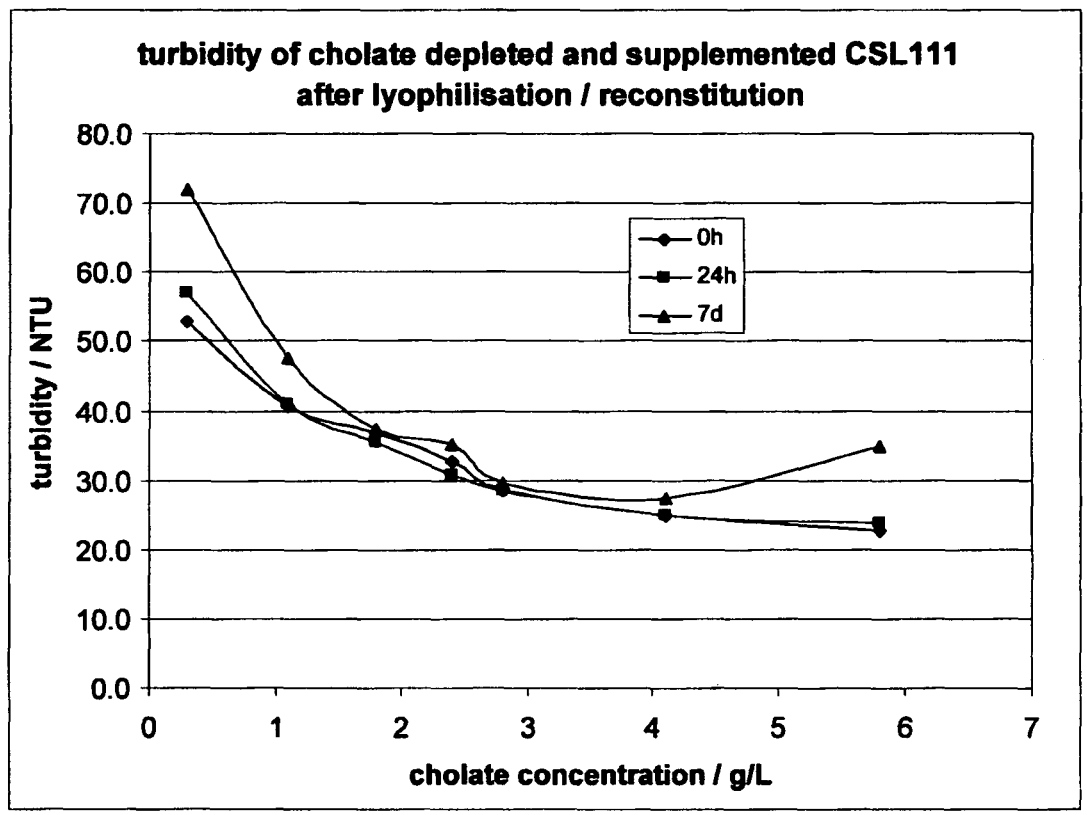
FIG. 4 shows results of turbidity of CSL111 in the presence of different concentrations of cholate after lyophilization and reconstitution.

These samples were then lyophilized and reconstituted. The turbidity was measured after 0 h, 24 h and 7 days of storage. The turbidity values after the lyophilization and reconstitution are higher than for the non-lyophilized samples (compare FIG. 3 and FIG. 4).

The reconstituted CSL111 particles appear to require a mimimum cholate concentration to remain stable. If the cholate concentration is too low, aggregates and tubidity develop. Also, the molecular size distribution changes faster at low cholate concentrations.

Figure 5:
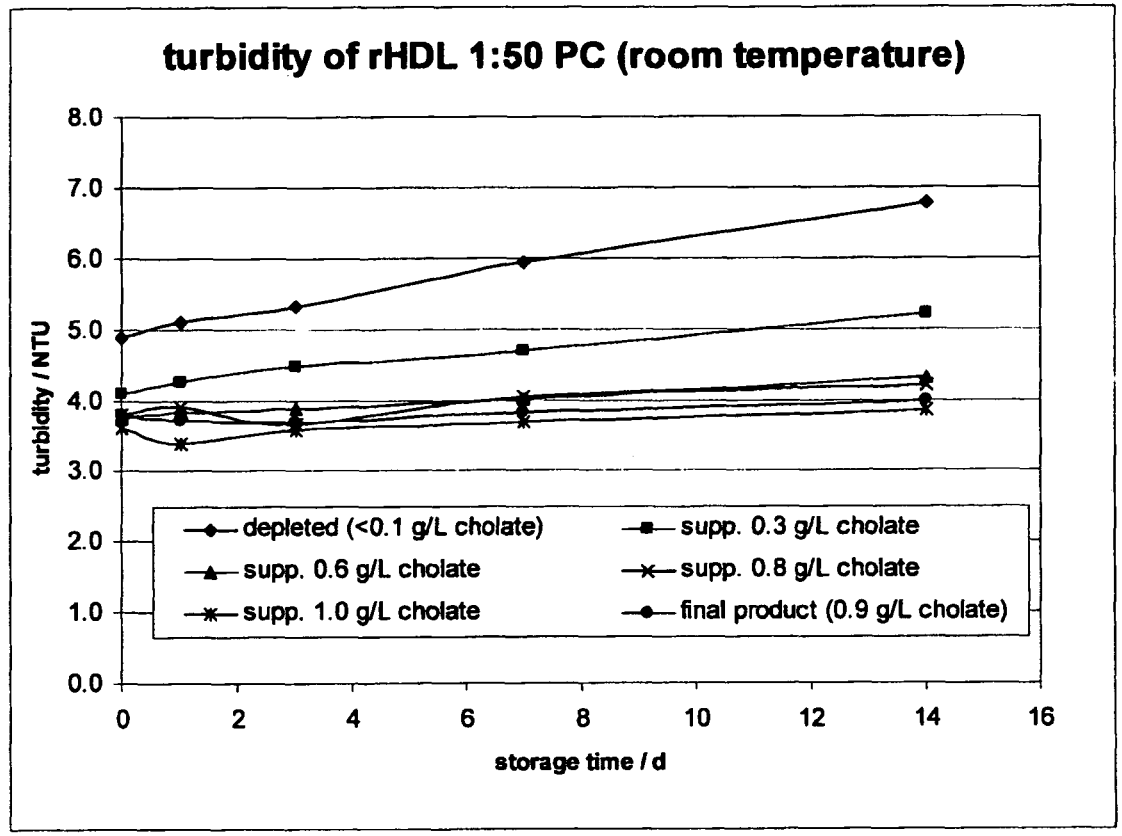
FIG. 5 shows results of turbidity analysis of reconstituted HDL 1:50 PC at room temperature (RT)
Figure 6:
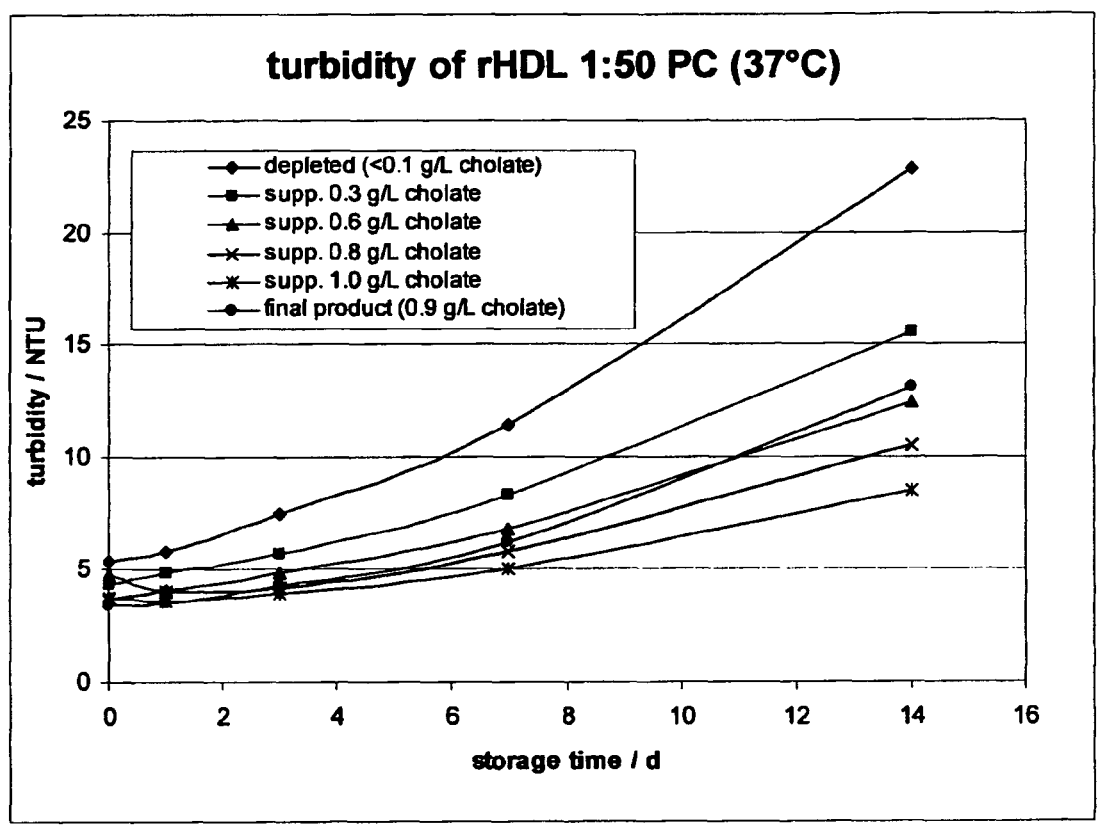
FIG. 6 shows results of turbidity analysis of reconstituted HDL 1:50 PC at 37° C.

Reconstituted HDL 1:50 PC
Data for turbidity are given in FIGS. 5 & 6.
The turbidity data indicated that the changes at RT are small for cholate concentrations ≥0.3 g/L.

The SE-HPLC chromatograms after 24 h at RT (not shown) demonstrated the same tendency as the turbidity values. With a cholate concentration of ≥0.3 g/L, the changes are small. Between 0.8-1.0 g/L, the chromatograms show almost no difference. Therefore it is not expected to obtain an increase in stability if the cholate concentration is increased above 1.0 g/L. For the 1:50 formulation with 20 g/L protein, a cholate concentration between 0.3-1.0 g/L is therefore regarded to be optimal. Calculated for a product containing 30 g/L protein, the optimal cholate concentration would range from 0.5-1.5 g/L.

Figure 7:
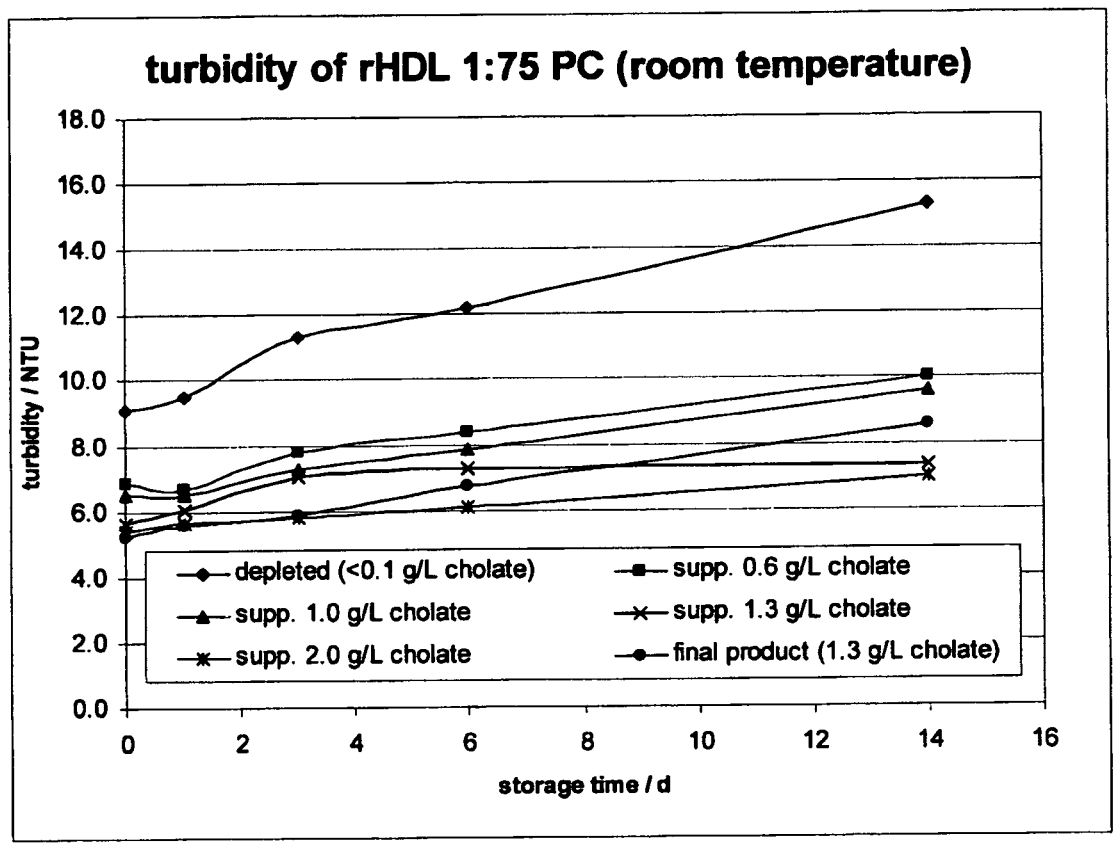
FIG. 7 shows results of turbidity analysis of reconstituted HDL 1:75 PC at RT.
Figure 8:
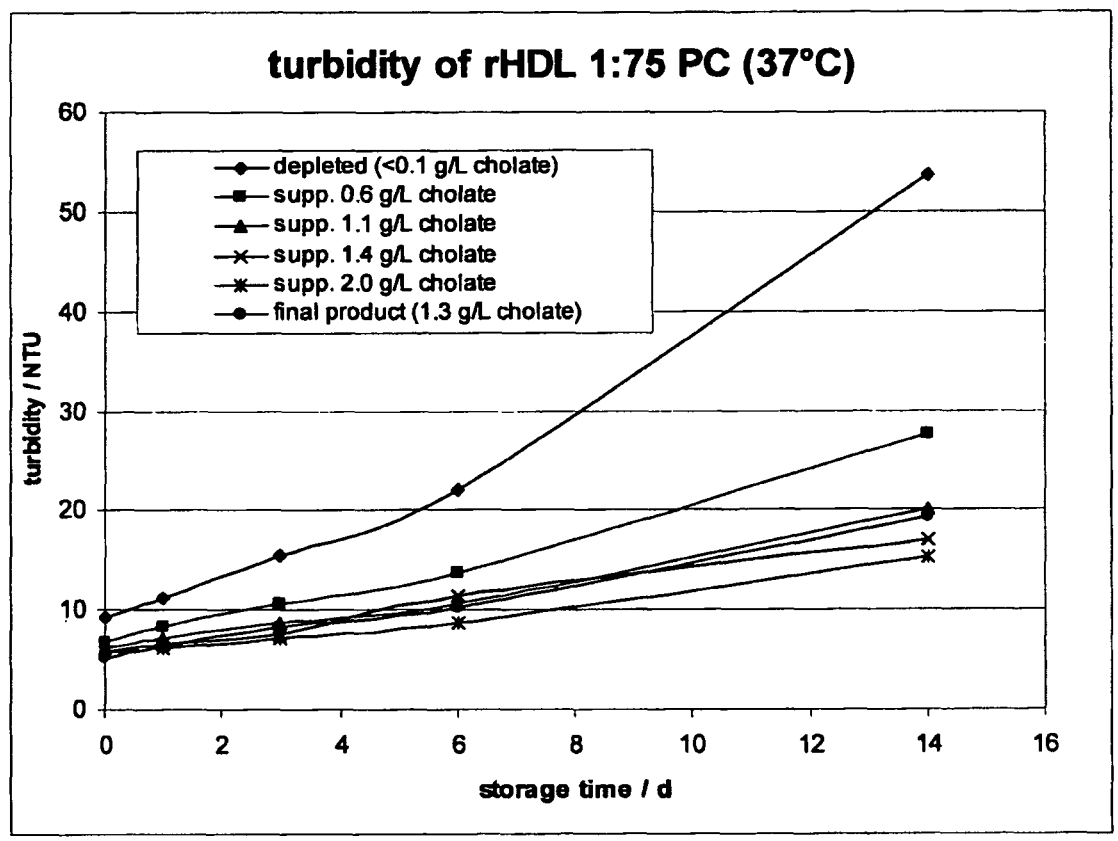
FIG. 8 shows results of turbidity analysis of reconstituted HDL 1:75 PC at 37° C.

Reconstituted HDL 1:75 PC
The turbidity measurements (FIGS. 7 & 8) of the 1:75 formulation show a clear increase for concentrations below 0.6 g/L cholate. Differences after one day of storage for the other concentrations (0.6-2.0 g/L cholate) are low.

The SE-HPLC chromatograms of the molecular size distribution after 24 hours at RT (not shown) showed a clear difference between the depleted and the other samples.

Between 1.0-1.3 g/L cholate, the chromatograms showed almost no difference. Therefore a large increase in stability for cholate concentrations above 1.3 g/L is not expected. For the 1:75 formulation with 20 g/L protein, a cholate concentration between 0.6-1.3 g/L is therefore regarded to be optimal. For a formulation with 30 g/L protein this equates to a 0.9-2.0 g/L final cholate concentration.

Conclusions
An optimal cholate concentration of 0.5-1.5 g/L was selected for the rHDL formulation of the invention. Below this range, the stability decreased. Cholate concentrations above 13 g/L caused a slight increase in stability. However, an appreciable increase in liver toxicity can be expected with higher cholate concentrations.

Example 4

Liver Toxicity Trial Comparison with CSL111

Introduction
The goal of this study was to confirm the favourable hepatotoxic profile of an embodiment of the rHDL formulation of the invention after intravenous infusion to rabbits. Hepatotoxicity is defined as increased liver enzyme (ALT) activity in serum. Apo-A1 is considered to be the active component of both formulations and plasma levels of Apo-A1 are the key indicator of exposure.

Materials & Methods
Administration of Test rHDL Formulations
Test rHDL Formulation 1
Substance/INN: rHDL CSL111
Manufacturer: CSL Behring AG, Bern
Lot number: E502-03750-00005
Dose: 75 mg/kg b.w.
Route: i.v.
Frequency: infusion t=0-40 min.
Application volume: 4.95 mL/kg/h
Test rHDL Formulation 2
Substance/INN: rHDL (PC 1:55)
Manufacturer: CSL Behring AG, Bern
Lot number: 1003.E009.01
Dose: 75 mg/kg b.w.
Route: i.v.
Frequency: infusion t=0-40 min
Application volume: 3.87 mL/kg/h
Study Design
This study was designed as an open two-armed trial in a total of 6 female rabbits. The dosing regimen is summarized in Table 5.

Treatment Groups

TABLE 5

Treatment groups

| No. | Treatment | Dose/volume/route | N (f) |
|---|---|---|---|
| 1 | rHDL CSL111 | 75 mg/kg b.w./4.95 mL/kg/h/i.v. | 3 |
| 2 | rHDL PC1:55 | 75 mg/kg b.w./3.87 mL/kg/h/i.v. | 3 |

Experimental Animals
Species: Rabbit
Strain: CHB
No. of animals, Sex: 6 (female)
Supply: Fa. Bauer (Neuenstein-Lohe, Germany)
Body weight: 3.1-3.3 kg
Age at arrival: about 3-4 months
Housing: wiresteel cages; 1 animal/cage
Bedding: no
Water: tap water, ad libitum
Food: Deukanin Pellets (Deuka), ad libitum
Light/darkness: 12 h/12 h
Temperature: 21-23° C.

Relative humidity: 50%

Animal Model

Animals were fixed in a restraint device (rabbit holder). An i.v. catheter was placed into the ear vein. Test articles were given as a 40 minutes i.v. infusion. Blood samples were taken from the ear artery and collected into serum and streptokinase-plasma (5%) vials. Blood samples were processed to serum, stored at −20° C. and to plasma and stored at −80° C.

Determination of Liver Enzymes

The samples were analyzed for ALT activity using enzymatic photometric test kits available commercially (Greiner Biochemica).

Determination of Apo A-I Plasma Level

The determination of human Apo A-I was performed by a nephelometric assay.

Results

Means and standard deviations of in vivo data are given in Tables 6 to 7.

The embodiment of the rHDL formulation tested herein did not increase ALT serum levels. CSL111 increased ALT from 25 U/L to 94 U/L at 8 h.

Peak levels of human Apo-AI were seen at time-point 40 min. for the rHDL forumation (1.5 mg/dL) and CSL111 (1.6 mg/dL).

TABLE 6

ALT serum levels (mean ± SD)
Treatment/Serum concentration (U/L)

| Time-point | rHDL CSL 111<br>75 mg/kg<br>n = 3 | rHDL PC 1:55<br>75 mg/kg<br>n = 3 |
|---|---|---|
| baseline | 25.38 ± 9.05 | 45.07 ± 4.77 |
| 40 min. | 35.62 ± 25.04 | 52.31 ± 16.21 |
| 2 h | 56.77 ± 28.77 | 49.05 ± 10.84 |
| 4 h | 63.65 ± 33.42 | 43.17 ± 11.53 |
| 8 h | 94.22 ± 58.63 | 33.26 ± 4.25 |

TABLE 7

Apo-A1 plasma levels (mean ± SD)
Treatment/Serum concentration (mg/dL)

| Time-point | rHDL CSL 111<br>75 mg/kg<br>n = 3 | rHDL PC 1:55<br>75 mg/kg<br>n = 3 |
|---|---|---|
| baseline | 0.000 ± 0.000 | 0.000 ± 0.000 |
| 40 min. | 1.571 ± 0.311 | 1.509 ± 0.481 |
| 2 h | 1.083 ± 0.323 | 1.203 ± 0.250 |
| 4 h | 0.939 ± 0.356 | 1.073 ± 0.164 |
| 8 h | 0.740 ± 0.260 | 0.830 ± 0.198 |

Example 5

The ability to make synthetic HDL particles of the invention was determined for particles containing lower phospholipid levels. The Apo A-I to phospholipid ratios ranged from 1:2 to 1:55.

To make the synthetic HDL particles, sodium cholate (New Zealand Pharmaceuticals) was dissolved in buffer (10 mM NaCl, 1 mM EDTA, 10 mM TRIS, pH 8.0) and stirred until clear. Soybean phosphatidyl-choline (Phospholipid GmbH) was added to an appropriate volume of the cholate and stirred for 16 h at room temperature. The apoA-I solution was diluted to a protein concentration of 9.0 g/L (determined by OD280) with 10 mM NaCl and mixed with an appropriate volume of the lipid solution to obtain the appropriate protein to lipid ratio. The mixture was stirred at 2-8° C. for 16 h. The HDL mimetics were prepared by cholate removal over a HiPrep 26/10 desalting column using 1% sucrose as running buffer. The eluate was concentrated by ultrafiltration to a protein concentration of 20 g/L and 7.5% sucrose, respectively.

The reconstituted HDL preparations were incubated (stored) at 2-8° C. and the following parameters were measured after 0, 5 and 14 days:

Transmission (405 nm), particle size distribution (SE-HPLC), endotoxins, SDS-PAGE (reducing and non-reducing), Native PAGE, LCAT activation, apoA-I concentration, and in-vitro toxicity At Day 0 the following additional tests were performed: i) protein concentration by modified Biuret adapted for lipid containing samples (deoxycholate was added to Biuret solution); ii) phosphatidyl-choline concentration (Propiagnostica mti-diagnostics GmbH); and iii) cholate concentration was measured by a colorimetric Gallsäuren test kit and Gallsäuren-Stoppreagens (Trinity Biotech).

Particle size distribution was determined by SE-HPLC using a Superose 6 10/300 GL column (GE Healthcare) with PBS+0.1% sodium azide as running buffer. The flow rate was 0.5 mL/min, 5 µL sample was injected, detection occurred at a wavelength of 280 nm. The synthetic HDL particles were analysed by SDS-PAGE (reducing/non-reducing) using the XCell SureLock Mini-Cell with NuPAGE Novex Bis-Tris Gels 4-12% and MOPS or MES electrophoresis buffer (Invitrogen). Protein bands were visualized with the Bio-Safe Coomassie Stain (Bio-Rad). Native PAGE was performed using the XCell SureLock Mini-Cell with Native Page Novex Bis-Tris Gels 4-16% and the NativePAGE Running Buffer Kit (Invitrogen). Protein bands were visualized with the GelCode Blue Stain Reagent (Thermo Scientific). The apoA-I concentration was determined by capillary electrophoresis using a 3D CE instrument (Agilent technologies) and an Extended Light Path CE capillary (50 µm, 56 cm, both Agilent Technologies). The electrophoresis buffer was 53 mM Na-Borat pH 9.1, 0.21% SDS, 5% methanol. Electrophoresis was run at 25 kV.

LCAT activity was determined in quadruplicate. Briefly, samples of 10 µL were pipetted in a chilled tube. 150 µL human plasma, 150 µL PBS and 20 µL 14 C cholesterol (Perkin Elmer) were dissolved in 25 mg/mL human albumin solution, mixed and incubated at 2-8° C. for 90 minutes. Duplicate samples were incubated at 37° C., the other 2 samples (blank) at 2-8° C. for 30 min. 2 mL ethanol was added to stop the reaction and subsequently extracted twice with hexane (1×5 mL, 1×3 mL). The hexane was evaporated to dryness and the residues redissolved in 0.5 mL hexane. The cholesterol ester was separated from the other substances by passing the extract through a solid phase Amino SPE column, eluting with 2×1 mL hexane. The radioactivity in the eluate was determined on a scintillation beta counter.

In-vitro toxicity involved preparing HEP-G2 cells (Day 1): a log-phase culture of HEP-G2 cells from one T75 flask was taken, the culture medium removed and the cells washed with PBS. After trypsinization and resuspension in 10 mL culture medium (90% DMEM, 10% inactivated FCS, 1% nonessential amino acids, 1% Pen/Strep) the concentration was determined by Neubauer/Trypan blue. 100 ul cells (10×104 C/mL)/well were seeded into 96 well F-bottom plates. The plate was incubated overnight at 37° C./5% $CO_2$, 95% $H_2O$. Incubation (Day 2): 700 µL sample of the highest compound concentration were prepared in culture medium. The medium from the first row of wells was removed and 200 ul of the solution added to the cells. A serial 1:2 dilution series was done and the plate was incubated during 72 hours at 37° C./5% $CO_2$, 95% $H_2O$. Viability (Day 3): 50 µL of 3× Neutral Red Solution (70 mg Neutral Red in 100 mL PBS) was added to each well. The plate was incubated for 2 hours at 37° C./5% $CO_2$, 95% $H_2O$ and the wells were washed once with 200 µL PBS/well, 100 µL ethanol was added to each well and the plate was put on a shaker for 20 minutes. The absorption in each well was read at 540 nm.

A summary of the characteristics of the synthetic HDL particles containing different ratios of phospholipid to protein are provided in Table 8. The % transmission indicates that the particles were stable. The LCAT values decreased as the level of phospholipid present in the synthetic particles was reduced. This is consistent with the phospholipid acting as a substrate for LCAT.

HPLC-SEC results indicated that particles with ratio's of 1:20 and 1:30 eluted as a single symmetrical peak. Synthetic HDL particles with lower levels of lipid to Apo A-I contained a shoulder that was more pronounced in the particles with ratio's of 1:5 and 1:2. In addition the elution time of the main peak was progressively later as the phospholipid to protein ratio was reduced. This indicates that the particles are becoming progressively smaller. This change of size was also reflected in the Native PAGE results where a low molecular weight band was observed at increasing intensity as the ratio was reduced 1:55 to 1:2. The SDS-PAGE was similar for all samples.

The in vitro assay results indicated that the cell viability for each preparation remained stable over the 14 day period. There was a small reduction in cell viability observed with increasing lipid levels when the cells were incubated with reconstituted HDL at the highest concentration (2 mg/mL) (See Table 9, below).

Example 6

The effect on toxicity of synthetic HDL particles reconstituted using different detergents was examined.

To make the particles Amberlite XAD-2 beads were cleaned by incubation in 20% methanol over night and subsequently sanitized by washing four times with 1 M sodium hydroxide and twice with ultrapure water. Before use the beads were washed with 7.5% sucrose and dried on a filter.

The synthetic HDL particles were made by the following method. Freeze dried HDL particles containing residual cholate were reconstituted with WFI to a protein concentration of 30 g/L. Amberlite XAD-2 beads (10 g per g of protein) were added to the reconstituted HDL preparation and incubated at 2-8° C. for 3.5 hours with shaking. After removal of the beads by filtration this procedure was repeated once more with another portion of Amberlite XAD-2 beads (10 g beads per g of protein). The beads were then removed by filtration and detergent (cholate, deoxycholate, octylglucoside, Polysorbate 80) added to obtain a final detergent concentration of 1 g/L or 6 g/L.

The samples were then tested for stability as determined in the Example above.

For the polysorbate 80 preparations the detergent level was determined by a photometric assay: The protein in 1000 µL sample was precipitated with 5 mL 0.1 M ammonium acetate ans sedimented by centrifugation. The supernatant was evaporated to dryness and re-dissolved in 1 ml sodium tetraborate buffer pH 9.1 (0.953 g sodium tetraborate ad 100 mL with H$_2$O, add 10 mL HCl), 4 ml TBPE-K solution (1.76 g

TABLE 8

Summary of characteristics of the synthetic HDL particles with different Apo A-I to phospholipid ratios (1:2 to 1:55).

| Sample | Time (days) | Apo A-I (mg/mL) | Protein (mg/mL) | Phospholipid (g/L) | Ratio | Cholate (g/L) | LCAT (% Ref) | Transmission (%) | Endotoxin (EU/mg) |
|---|---|---|---|---|---|---|---|---|---|
| 1:55 | t = 0 | 21.00 | 20.4 | 33.3 | 59 | 1.4 | 78 | 72.3 | 3.0 |
|  | t = 5 | — | — | — | — | — | 82 | 70.6 | 3.2 |
|  | t = 14 | 20.74 | — | — | — | — | 81 | 70.6 | 5.4 |
| 1:40 | t = 0 | 20.60 | 20.0 | 21.9 | 39 | 0.8 | 51 | 73.9 | 2.4 |
|  | t = 5 | — | — | — | — | — | 53 | 72.3 | 2.7 |
|  | t = 14 | 21.93 | — | — | — | — | 52 | 72.2 | 2.4 |
| 1:30 | t = 0 | 19.79 | 19.7 | 16.3 | 30 | 0.4 | 37 | 75.7 | 2.1 |
|  | t = 5 | — | — | — | — | — | 41 | 74.1 | 10.1 |
|  | t = 14 | 20.75 | — | — | — | — | 39 | 74.0 | 2.9 |
| 1:20 | t = 0 | 18.34 | 19.7 | 10.9 | 20 | 0.1 | 28 | 76.8 | 0.8 |
|  | t = 5 | — | — | — | — | — | 33 | 74.8 | 11.6 |
|  | t = 14 | 19.32 | — | — | — | — | 29 | 75.0 | 1.9 |
| 1:10 | t = 0 | 16.21 | 19.8 | 5.4 | 10 | <0.1 | 27 | 76.3 | 3.3 |
|  | t = 5 | — | — | — | — | — | 26 | 76.5 | 2.1 |
|  | t = 14 | 16.33 | — | — | — | — | 24 | 76.2 | 2.5 |
| 1:5 | t = 0 | 15.15 | 18.7 | 2.8 | 5 | <0.1 | 23 | 77.0 | 1.9 |
|  | t = 5 | — | — | — | — | — | 23 | 77.2 | 1.4 |
|  | t = 14 | 16.97 | — | — | — | — | 20 | 75.9 | 1.4 |
| 1:2 | t = 0 | 14.06 | 17.5 | 1.0 | 2 | <0.1 | 20 | 77.6 | 1.6 |
|  | t = 5 | — | — | — | — | — | 20 | 77.8 | 1.1 |
|  | t = 14 | 14.59 | — | — | — | — | 17 | 77.3 | 0.8 |

* Blank cells indicate that data was not obtained.

TABLE 9

Summary of % viability of the synthetic HDL particles with different Apo A-I to phospholipid ratios (1:2 to 1:55).

|  | HDL Conc. (mg/mL) | 1:2 | 1:5 | 1:10 | 1:20 | 1:30 | 1:40 | 1:55 |
|---|---|---|---|---|---|---|---|---|
| 0 days | 0.5 | 97 | 87 | 104 | 95 | 97 | 109 | 97 |
|  | 1.0 | 105 | 96 | 110 | 101 | 109 | 100 | 105 |
|  | 2.0 | 101 | 84 | 86 | 93 | 87 | 76 | 77 |
| 5 days | 0.5 | 98 | 89 | 102 | 102 | 100 | 111 | 97 |
|  | 1.0 | 105 | 100 | 110 | 107 | 108 | 110 | 105 |
|  | 2.0 | 97 | 87 | 89 | 93 | 94 | 81 | 78 |
| 14 days | 0.5 | 97 | 96 | 107 | 103 | 103 | 112 | 103 |
|  | 1.0 | 106 | 99 | 113 | 107 | 111 | 112 | 106 |
|  | 2.0 | 95 | 86 | 91 | 97 | 100 | 91 | 78 | potassium chloride, 0.48 g sodium tetraborate, 4800 μL 0.1 M KOH, 0.015 g TBPE-K in 5 mL ethanol, ad 100 mL with H2O) added and extracted with 2.5 ml dichloromethane on a end-over-end mixer for 30 min. After phase separation the absorption of the dichloromethane phase was measured at 611 nm (reference wavelength 700 nm).

A summary of the characteristics of the synthetic HDL particles containing different ratio's of phospholipid to protein are provided in Table 10. The % transmission and LCAT values indicate that the particles were stable and functional.

HPLC-SEC results indicated that particles with the different detergents eluted as a single symmetrical peak. This was also reflected in the band patterns observed in the Native PAGE. The SDS-PAGE was similar for all samples. The in vitro assay results indicated that the cell viability varied depending on the level of detergent present. In particular high detergent levels resulted in reduced cell viability. The values however remained stable over the 14 day period (See Table 11).

TABLE 10

Summary of characteristics of the synthetic HDL particles with different detergents.

| Sample | Time (days) | Apo A-I (mg/mL) | Protein (mg/mL) | Phospholipid (g/L) | Ratio | Cholate (g/L) | LCAT (% Ref) | LCAT | Transmission | Endotoxin (EU/mg) |
|---|---|---|---|---|---|---|---|---|---|---|
| Polysorbate 1 g/L | t = 0 | 21.24 | 20.98 | 37.28 | 64 | — | 97 | 83 | 65.4 | 0.0 |
|  | t = 5 | — | — | — | — | — | 97 | 80 | 62.9 | 0.0 |
|  | t = 14 | 22.07 | — | — | — | — | 103 | 82 | 65.6 | 0.0 |
| Polysorbate 6 g/L | t = 0 | 21.42 | 21.09 | 38.10 | 65 | — | 108 | 85 | 63.8 | 0.0 |
|  | t = 5 | — | — | — | — | — | 114 | 83 | 59.2 | 0.1 |
|  | t = 14 | 20.71 | — | — | — | — | 131 | 94 | 63.9 | 0.0 |
| Deoxycholate 1 g/L | t = 0 | 21.26 | 20.94 | 36.42 | 63 | 1.3 | 104 | 86 | 68.5 | 0.0 |
|  | t = 5 | — | — | — | — | — | 103 | 89 | 65.8 | 0.0 |
|  | t = 14 | 23.08 | — | — | — | — | 113 | 89 | 66.2 | 0.1 |
| Deoxycholate 6 g/L | t = 0 | 19.79 | 21.39 | 37.92 | 64 | 6.1 | 113 | 101 | 69.0 | 0.0 |
|  | t = 5 | — | — | — | — | — | 118 | 101 | 65.8 | 0.0 |
|  | t = 14 | 20.63 | — | — | — | — | 126 | 103 | 64.1 | 0.0 |
| Octylglucoside 1 g/L | t = 0 | 16.33 | 21.39 | 35.38 | 60 | — | 91 | 80 | 63.4 | 0.0 |
|  | t = 5 | — | — | — | — | — | 94 | 80 | 57.8 | 0.0 |
|  | t = 14 | 22.34 | — | — | — | — | 99 | 81 | 62.7 | 0.0 |
| Octylglucoside 6 g/L | t = 0 | 20.75 | 20.94 | 35.66 | 62 | — | 113 | 93 | 62.4 | 0.0 |
|  | t = 5 | — | — | — | — | — | 115 | 94 | 59.4 | 0.0 |
|  | t = 14 | 21.9 | — | — | — | — | 127 | 102 | 55.9 | 0.0 |
| Cholate 1 g/L | t = 0 | 22.25 | 21.24 | 36.52 | 62 | 1.4 | 101 | 88 | 68.2 | 0.0 |
|  | t = 5 | — | — | — | — | — | 106 | 90 | 65.6 | 0.1 |
|  | t = 14 | 22.54 | — | — | — | — | 115 | 86 | 66.4 | 0.0 |
| Cholate 6 g/L | t = 0 | 21.54 | 21.13 | 34.66 | 59 | 7.2 | 122 | 106 | 67.8 | 0.0 |
|  | t = 5 | — | — | — | — | — | 130 | 103 | 66.3 | 0.0 |
|  | t = 14 | 22.43 | — | — | — | — | 140 | 114 | 63.1 | 0.0 |

* Blank cells indicate that data was not obtained.

TABLE 11

Summary of % viability of the synthetic HDL particles in the presence of different detergents.

| Day | HDL Conc. (mg/mL) | Cholate (1 g/L) | Cholate (6 g/L) | Octylglucoside (1 g/L) | Octylglucoside (6 g/L) | Deoxycholate (1 g/L) | Deoxylcholate (6 g/L) | PS80 (1 g/L) | PS80 (6 g/L) |
|---|---|---|---|---|---|---|---|---|---|
| 0 | 0.5 | 90 | 90 | 99 | 56 | 98 | 32 | 95 | 74 |
|  | 1.0 | 81 | 72 | 86 | 21 | 76 | 7 | 79 | 31 |
|  | 2.0 | 55 | 32 | 26 | 5 | 39 | 5 | 43 | 7 |
| 5 | 0.5 | 88 | 90 | 103 | 56 | 95 | 35 | 97 | 73 |
|  | 1.0 | 80 | 68 | 88 | 18 | 75 | 6 | 83 | 25 |
|  | 2.0 | 58 | 30 | 35 | 5 | 44 | 5 | 41 | 5 |
| 14 | 0.5 | 91 | 92 | 89 | 56 | 96 | 32 | 95 | 72 |
|  | 1.0 | 84 | 70 | 86 | 17 | 76 | 10 | 85 | 23 |
|  | 2.0 | 56 | 31 | 49 | 5 | 40 | 5 | 44 | 5 |

Example 7

The synthetic HDL particles were made as described in Example 5 above with the exception that POPC (NOF Corporation) was used to reconstitute the HDL particles. The particles were then examined by the methods described in Example 5.

Results indicate a stable/functional product which exhibits similar toxicity properties to synthetic HDL particles reconstituted with Soybean phosphatidylcholine (Tables 12 & 13).

TABLE 12

Summary of characteristics of the synthetic HDL particles

| Sample | Time (days) | Apo A-I (mg/mL) | Protein (mg/mL) | Phospholipid (g/L) | Ratio | Cholate (g/L) | LCAT (% Ref) | Transmission (%) |
|---|---|---|---|---|---|---|---|---|
| PC, 1:55 | t = 0 | 23.27 | 23.1 | 32.1 | 50 | 1.2 | 85 | 69.7 |
|  | t = 5 | — | — | — | — | — | 83 | 69.9 |
|  | t = 14 | 20.90 | — | — | — | — | 87 | 69.9 |
| POPC, 1:55 | t = 0 | 21.55 | 22.1 | 30.4 | 50 | 1.2 | 151 | 72.0 |
|  | t = 5 | — | — | — | — | — | 145 | 73.0 |
|  | t = 14 | 19.90 | — | — | — | — | 149 | 72.2 |

* Blank cells indicate that data was not obtained.

TABLE 13

Summary of % viability of the synthetic HDL particles in the presence of different phospholipids.

|  | HDL Conc. (mg/mL) | Soy bean PC | POPC |
|---|---|---|---|
| 0 days | 0.5 | 102 | 101 |
|  | 1.0 | 97 | 101 |
|  | 2.0 | 63 | 63 |
| 5 days | 0.5 | 104 | 113 |
|  | 1.0 | 96 | 99 |
|  | 2.0 | 62 | 59 |
| 14 days | 0.5 | 105 | 112 |
|  | 1.0 | 96 | 92 |
|  | 2.0 | 60 | 53 |

Example 8

The safety and tolerability and the pharmacokinetics of escalating doses of the reconstituted HDL formulations of the invention can be assessed by either single or multiple intravenous infusions in healthy volunteers. The study has two arms with one involving the use of the synthetic HDL particles in escalating doses and the other involving the use of a normal saline (0.9%) placebo comparator. The infusions will be randomized and double blinded (Subject, Investigator and Outcomes assessor).

The healthy volunteers can be either male or female aged from 18 years to 55 years and weighing at least 45 kg. Other entry criteria can include a body mass index (BMI) of between 18 and 42.0 kg/m$^2$. Exclusion criteria can include i) evidence of a clinically significant medical condition, disorder or disease; ii) evidence of hepatobiliary disease; iii) evidence of clinically relevant abnormal laboratory test result; and iv) evidence of history of alcohol or substance abuse.

Safety and tolerability will be measured by i) the frequency of drug related clinical adverse events up to 14 days after infusion; and ii) measuring liver function tests up to 14 days after infusion (eg. elevation of alanine aminotransferase (ALT) or aspartate aminotransferase (AST)). The pharmacokinetic information can be measured up to 10 days after infusion of the synthetic HDL particles. Particular measurements will include determining the plasma levels of lipoprotein.

CONCLUSION

Embodiments of a rHDL formulation of the invention and a CSL111 formulation have been evaluated to test whether rHDL formulation of the invention has an improved toxicity profile but preserved biological activity. The rHDL formulation of the invention has a reduced Apo-AI to PC ratio of 1:40 or 1:55 whereas CSL111 has a ratio of 1:150. In addition further purification efforts have lead to a substantial reduction of cholate in the formulation. As a consequence the rHDL formulation of the invention exhibits a reduced hepatic toxicity compared to CSL111. Importantly, the serum levels of Apo-AI were similar for both formulations, indicating similar exposure to the active component (see Table 7).

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A reconstituted high density lipoprotein (rHDL) formulation comprising an apolipoprotein; a lipid; and a detergent at a level selected from the group consisting of about 0.5-1.5 g/L and about 0.010-0.030 g/g apolipoprotein; wherein the apolipoprotein is Apo-A1, the lipid is phosphatidylcholine, and the detergent is sodium cholate.

2. The rHDL formulation of claim 1 wherein the level of detergent is about 0.5-1.5 g/L.

3. The rHDL formulation of claim 1, wherein the level of detergent is about 0.015-0.030 g/g apolipoprotein.

4. The rHDL formulation of claim 1, wherein the formulation further comprises a stabilizer.

5. A method of producing a rHDL formulation comprising an apolipoprotein; a lipid; and a detergent, said method including the step of providing said detergent at a level selected from the group consisting of about 0.5-1.5 g/L and about 0.010-0.030 g/g apolipoprotein; wherein the apolipoprotein is Apo-A1, the lipid is phosphatidylcholine, and the detergent is sodium cholate.

6. The method of claim 5, wherein the level of detergent is about 0.5-1.5 g/L.

7. The method of claim 5, wherein the level of detergent is about 0.015-0.030 g/g apolipoprotein.

8. The method of claim 5, including the steps of:
(A) adding phosphatidylcholine without organic solvent and a cholate detergent to an Apo-A1 solution;
(B) reducing the level of cholate detergent in the solution produced at step (I) to about 0.03 g/g Apo-A1;
(C) adding a stabilizer to the solution at step (B).

9. A rHDL formulation obtainable according to the method of claim 5.

10. A method of treating a disease, disorder or condition selected from the group consisting of one or more of cardiovascular disease, hypercholesterolaemia or hypocholesterolaemia in a human including the step of administering to the human a rHDL formulation, to thereby treat said disease, disorder or condition in the human; wherein the rHDL formulation comprises an apolipoprotein or fragment thereof; a lipid; and a detergent at a level selected from the group consisting of about 0.5-1.5 g/L and about 0.010-0.030 g/g apolipoprotein.

11. The method of claim 10, wherein the disease, disorder or condition includes acute coronary syndrome (ACS), atherosclerosis and myocardial infarction.

* * * * *